(12) United States Patent
Petty, Jr. et al.

(10) Patent No.: US 10,746,632 B2
(45) Date of Patent: Aug. 18, 2020

(54) AUTOMATED PLANT PRODUCT SAMPLER

(71) Applicant: Monsanto Technology LLC, St. Louis, MO (US)

(72) Inventors: Danny Michael Petty, Jr., St. Louis, MO (US); Tedman William Ahrens, St. Louis, MO (US); Lance Eric Layton, St. Louis, MO (US); Jamie Lee Ayers, St. Louis, MO (US); Douglas James Brune, St. Louis, MO (US); Jared Lee Pounds, St. Louis, MO (US); Luke Wayne Carpenter, St. Louis, MO (US); Chet Matthew Barber, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 248 days.

(21) Appl. No.: 15/755,012

(22) PCT Filed: Aug. 10, 2016

(86) PCT No.: PCT/US2016/046280
§ 371 (c)(1),
(2) Date: Feb. 23, 2018

(87) PCT Pub. No.: WO2017/034799
PCT Pub. Date: Mar. 2, 2017

(65) Prior Publication Data
US 2019/0368975 A1     Dec. 5, 2019

Related U.S. Application Data

(60) Provisional application No. 62/210,237, filed on Aug. 26, 2015.

(51) Int. Cl.
*G01N 1/02* (2006.01)
*G01N 1/18* (2006.01)
(Continued)

(52) U.S. Cl.
CPC ............. *G01N 1/02* (2013.01); *A01D 93/00* (2013.01); *G01N 1/08* (2013.01); *G01N 1/18* (2013.01);
(Continued)

(58) Field of Classification Search
CPC .. G01N 1/02; G01N 1/20; G01N 1/08; G01N 1/18; G01N 33/025; G01N 2001/021; A01D 93/00; A01D 46/08; A01D 46/085
See application file for complete search history.

(56) References Cited

U.S. PATENT DOCUMENTS

| | | | |
|---|---|---|---|
| 4,597,252 A * | 7/1986 | Williames | A01D 47/00 56/13.1 |
| 5,327,708 A | 7/1994 | Gerrish | |

(Continued)

FOREIGN PATENT DOCUMENTS

WO    2016025848 A1    2/2016
WO    2016049408 A1    3/2016

OTHER PUBLICATIONS

International Search Report from corresponding PCT/US2016/046280 dated Oct. 26, 2016.

*Primary Examiner* — Suman K Nath
(74) *Attorney, Agent, or Firm* — Sandberg Phoenix & von Gontard, P.C.

(57) ABSTRACT

A system for sampling of plant product is provided that comprises a mobile platform, at least one primary bin, and a harvesting subsystem connected to the mobile platform. The harvesting subsystem harvests the plant product as the system traverses a plot and projects it across the length of the primary bin(s) against a back wall of the primary bin(s), whereby the separated plant products collides with the back wall and falls into the primary bin. The system additionally includes at least one sample volumizer connected to the back wall of each primary bin. Each sample volumizer has a (Continued)

specified fixed volume and receives and collects a sample of the plant product, wherein each collected sample collected has the specified fixed volume. The system further includes at least one sample receiving subsystem structured and operable to receive and collect a sample from a respective sample volumizer.

28 Claims, 7 Drawing Sheets

(51) Int. Cl.
- *A01D 93/00* (2009.01)
- *G01N 1/08* (2006.01)
- *G01N 33/02* (2006.01)
- *A01D 46/08* (2006.01)

(52) U.S. Cl.
CPC .......... *G01N 33/025* (2013.01); *A01D 46/08* (2013.01); *G01N 2001/021* (2013.01)

(56) References Cited

U.S. PATENT DOCUMENTS

| | | |
|---|---|---|
| 6,119,531 A | 9/2000 | Wendte et al. |
| 6,422,937 B1 | 7/2002 | McLeod et al. |
| 6,559,655 B1 | 5/2003 | Rosenthal et al. |
| 7,434,375 B2 | 10/2008 | Pickett et al. |
| 8,082,809 B2 | 12/2011 | Luellen et al. |
| 2004/0063478 A1 | 4/2004 | Kormann et al. |

* cited by examiner

AUTOMATED PLANT PRODUCT SAMPLER

CROSS-REFERENCE TO RELATED APPLICATIONS

This application is a National Stage of International Application No. PCT/US2016/046280, filed Aug. 10, 2016, which claims priority to U.S. Provisional Application No. 62/210,237, filed on Aug. 26, 2015, the disclosures of which are incorporated herein by reference in its entirety.

FIELD

The present teachings relate to systems and methods for high-throughput sampling of a plant product, e.g., cotton. More particularly, the present teachings relate to systems and methods for high-throughput collection of plant product samples during the harvesting of one or more plots, wherein each sample collected has a fixed volume and is a random sample of the total plant product harvested.

BACKGROUND

The statements in this section merely provide background information related to the present disclosure and may not constitute prior art.

In crop analytics and plant breeding, researchers often need to collect samples of a plant product, e.g., tissues, seeds, fiber, leaves, roots, etc. in order to assess and compare crop performance of certain germplasms growing in certain plots. When collecting samples, researchers aim to reduce errors in at least four different ways: 1) by ensuring identity preservation, i.e. that each plot is accurately identified and that the identity of the sample collected accurately corresponds to its respective plot identity (e.g. that the contents of each sample are labeled accurately and in a trackable way), 2) by ensuring that each sample is free from contamination from other plots, 3) by ensuring that the sample collected from a plot accurately reflects the characteristics that the plant product is likely to exhibit when produced in a commercial setting, and 4) by ensuring that all samples are collected in a uniform manner.

Current sample collection methods include sending teams of human collectors into the field to collect samples directly by hand or by using hand-held tools, but these approaches are fraught with issues. For one, human collectors occasionally misidentify plots and/or mislabel collected samples, leading to spurious data and inaccurate selection decisions. Also, the samples that humans collect tend to over represent the plant product produced at the easiest to reach places on a plant, which can lead to samples that do not reflect what a grower and/or customer is likely to experience under commercial settings, e.g., when using a mechanized commercial harvester. Furthermore, since it is very difficult for any single human to collect plant product samples from different plots in exactly the same way, it is easy to understand why variations in the way samples are collected are unavoidable when the same person is collecting several dozen samples at a time, and even more so as the number of samples a single person collects climbs to the hundreds or thousands in a day. This lack of sample collection uniformity is exacerbated in global industrial plant breeding programs which routinely attempt to compare the performance of plants based on the properties of plant product samples collected on different days by different people in different parts of the world. Under such considerations, the limitations of human collection teams reliably collecting uniform samples become clear.

For example, cotton bolls are known to mature at different rates depending on where they are on the plant, i.e., the bolls at the bottom of the plant will tend to be more mature, and thus exhibit different yield and quality, than those growing from the top of the plant. Generally, such boll maturity distribution does not matter to the grower because typical commercial-grade cotton harvesters reliably collect all the bolls on each plant, so the final assessment as to the value of the crop is based on the combined quality of cotton each entire plant produces. However, cotton breeders generally do not want the sample to contain cotton from all the plants in a plot for two reasons: 1) the cotton produced by plants growing near alleyways will not reflect the characteristics that that a grower should expect from that variety because those plants face less competition for light and other resources due to the presence of alleys at the end of each plot; and 2) occasional contamination is expected to occur between some adjacent plots in the same row because the end plants often become so overgrown that some overlap is bound to occur.

Additionally, in some crop species, including cotton, the true variation in performance between plants in a plot can be low enough that samples collected from one, two, three or more plants growing in the middle of a particular plot can be considered representative of that entire plot. For example, when breeders sample cotton from a plot to compare the performance of germplasms, often they will focus collecting samples from only those plants growing in the middle of each plot.

Therefore, known methods for collecting samples of a particular plant product, e.g., seed cotton samples, inherently produce experimental errors and inefficiently collect plant products, especially in research settings.

SUMMARY

The present disclosure provides automated systems and methods for accurately and uniformly collecting a specified quantity of a plant product from a plot. For example, the present disclosure provides a high-throughput sampling system that functions automatically to collect plant product samples, e.g., cotton boll samples from a growing area comprising at least two different plots. In various embodiments, the systems and methods disclosed herein 1) ensure the contents of each plot in the growing area are accurately identified when samples are collected and that the identity of the plot are faithfully transferred to, and associated with, the corresponding sample(s) derived from them, 2) ensure that each sample is collected from plants growing near the middle of the plot where contamination from adjacent plots is less likely and where the population density (and thus the properties of the plant product produced there) more closely resembles that of a commercial production field, 3) ensure that the samples contain plant product samples from all parts of the plant with approximately equal probability, and 4) ensure that each sample is collected in a substantially identical manner e.g. that each sample contains approximately the same quantity of plant product and that each sample is handled, processed and/or analyzed in a substantially identical manner.

In various embodiments, the sampling system includes a mobile platform, such as a cotton harvester, at least one harvesting head, at least one harvest transport duct, and at least one sample volumizer structured and operable for collecting a specified volume of desired plant product. Each harvesting head separates plant products from a plurality of plants in a plot as the sampling system traverses the plot.

The at least one sample volumizer receives and collects a sample of the plant product that is conveyed by the harvest transport duct. In various embodiments, the volume of sample collected can be adjusted by changing the volume of the volumizer such that a specific volume of sample can be collected from at least one specific plot. In various embodiments, the volume of the volumizer can be set to remain fixed between adjacent plots, e.g. so that at least two samples of the same size can be collected from at least two adjacent plots. In various embodiments, the sampling system further includes at least one sample receiving subsystem, wherein each sample receiving subsystem is connected to a sample transport duct. Each sample receiving subsystem can receive and collect at least one sample from the respective sample volumizer.

The disclosed automated sampling system allows a single operator to rapidly and reliably collect a specific volume of contamination-free plant product representing only those plants growing in conditions closely approximating a commercial setting, i.e. from the middle of the plot. The sampling system does this by automatically coordinating the automated operations of the system with the geospatial position of the mobile platform within the respective field. For example, when the system reaches the middle of a plot, a computer based control system automatically harvests plant product(s) and collects the sample(s) in the sample volumizer. The harvesting of the plant product and the collecting the sample(s) can be initiated by a human operator, and/or based on the geospatial position of the mobile platform, and/or based on coordinates established for the field and the plot it contains, and/or based on any type of electronic instructions stored within the system and/or electronic instructions sent to the system, wirelessly or otherwise. In various embodiments, harvesting and/or collecting of the sample(s) is initiated once the mobile platform reaches a certain speed. For example, a user can program the computer controller of the sampling system to automatically initiate harvesting once the mobile platform has reached a certain speed, which a user can calibrate, such that the harvesting of an entire field of plots is reliably initiated near the middle of each plot. Or, for example, if the mobile platform halts its movement across the field just before the first plant in each plot, then it is possible to program the computer controller to automatically initiate harvesting once the mobile platform has advanced into the next plot and reached a certain speed, which a user can calibrate such that the harvesting is initiated near the middle of each plot.

The presently disclosed automated systems and methods drastically reduce experimental error resulting from variations in the way plant product is collected among different plots, and/or at different times, and/or at different locations, and/or with different human operators. For example, the quantity of sample collected can be calibrated such that every sample collected will comprise substantially the same quantity of cotton even when the yield of different plots varies widely.

This present disclosure anticipates a fully automated sample receiving subsystem that receives each sample from the volumizer(s), and automatically collects and labels each sample with identification label.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

Figure 1:
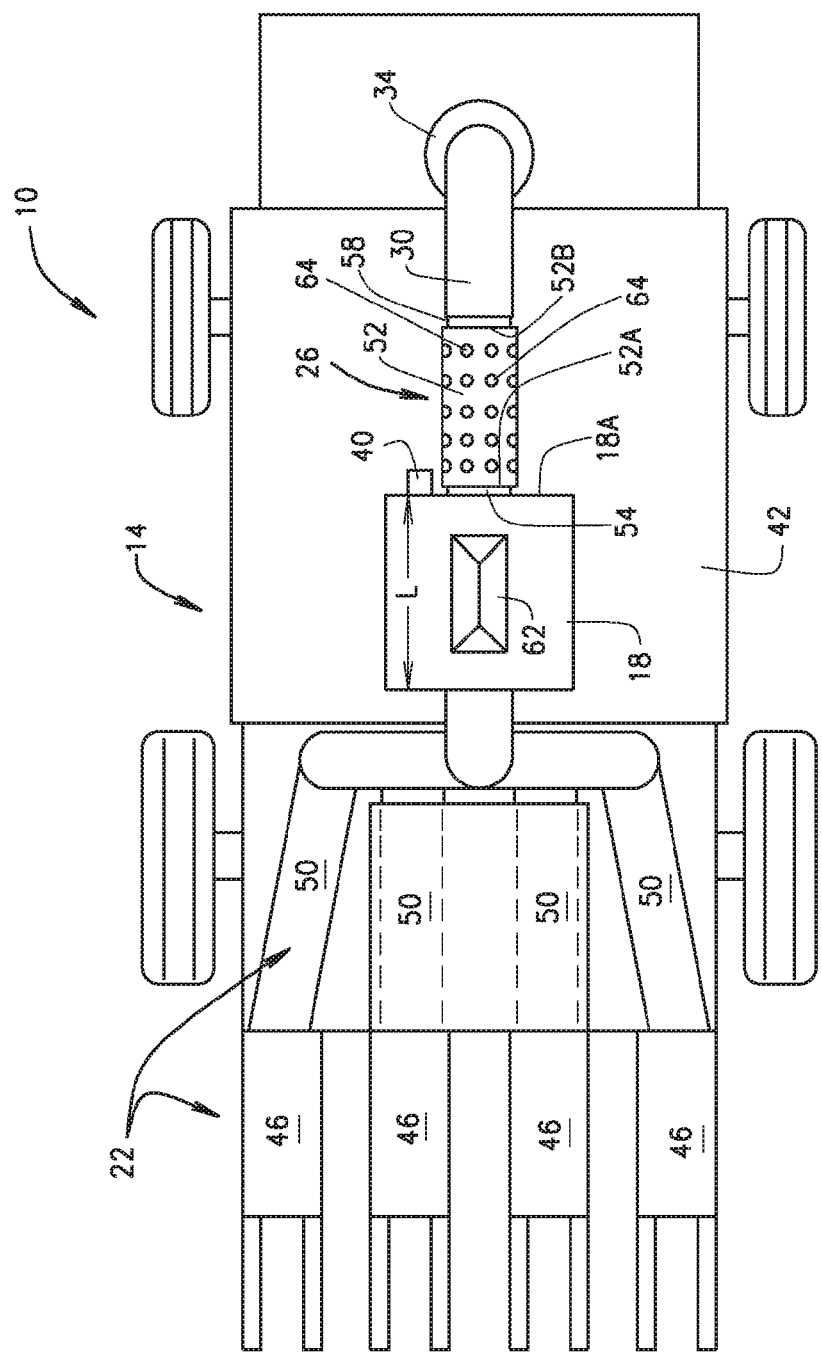
FIG. 1 is a block diagram of a high-throughput sampling system, in accordance with various embodiments of the present disclosure.
Figure 3:
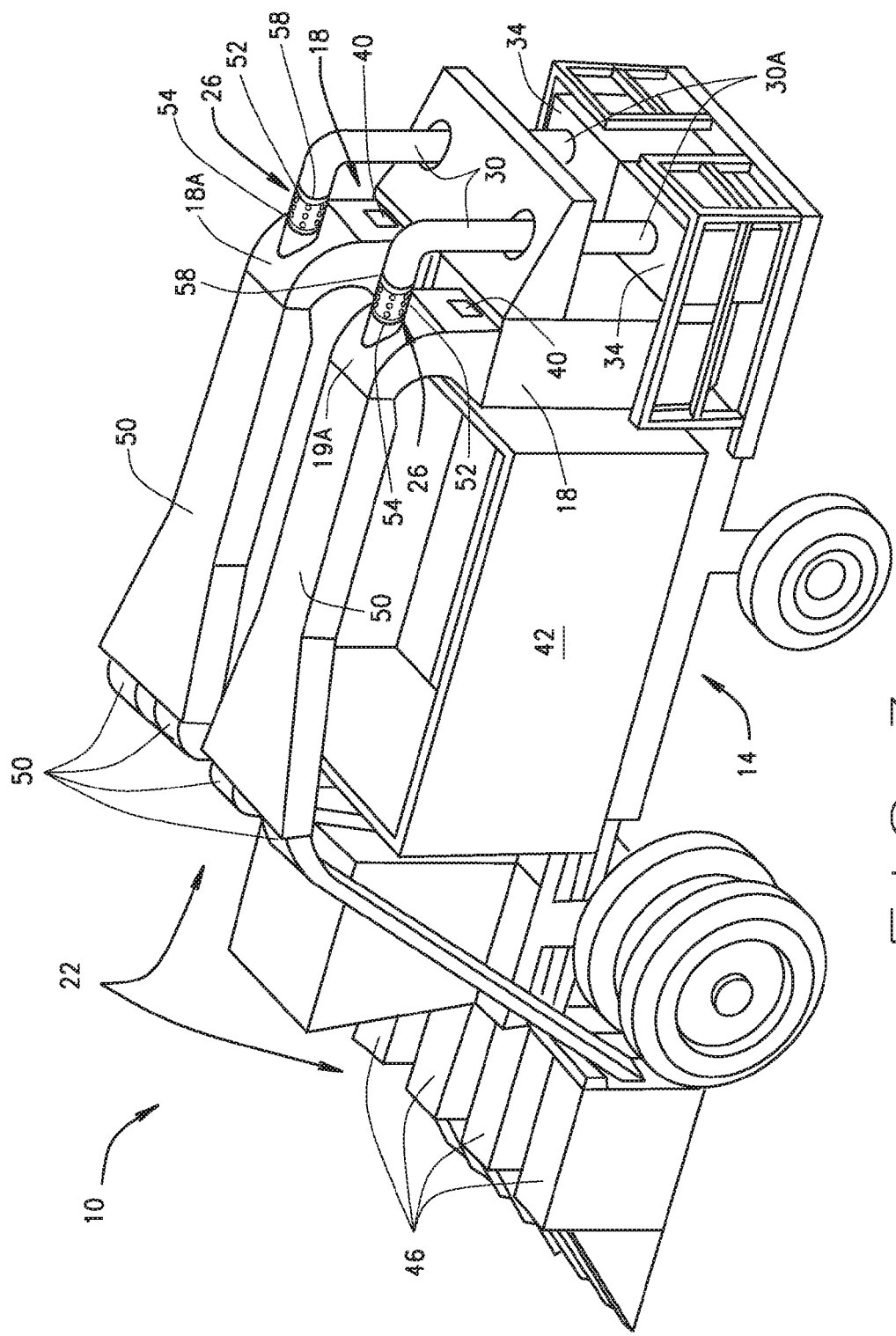

FIG. 3 an isometric view of the system shown in FIG. 1 in accordance with various other embodiments of the present disclosure.

Figure 4:
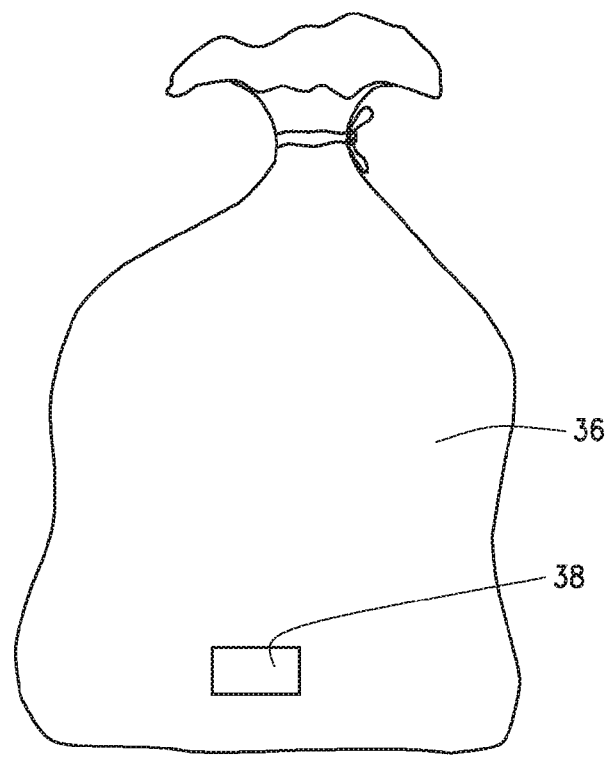

FIG. 4 is an exemplary illustration of a sample receptacle of the high-throughput sampling system shown in FIG. 1, in accordance with various embodiments of the present disclosure.

Figure 5:
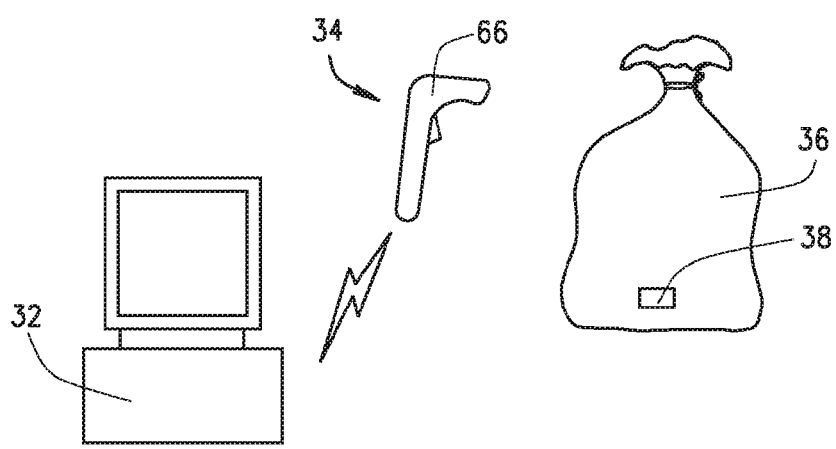

FIG. 5 is an exemplary illustration of a sample receiving subsystem of the high-throughput sampling system shown in FIG. 1, in accordance with various embodiments of the present disclosure.

Figure 6:
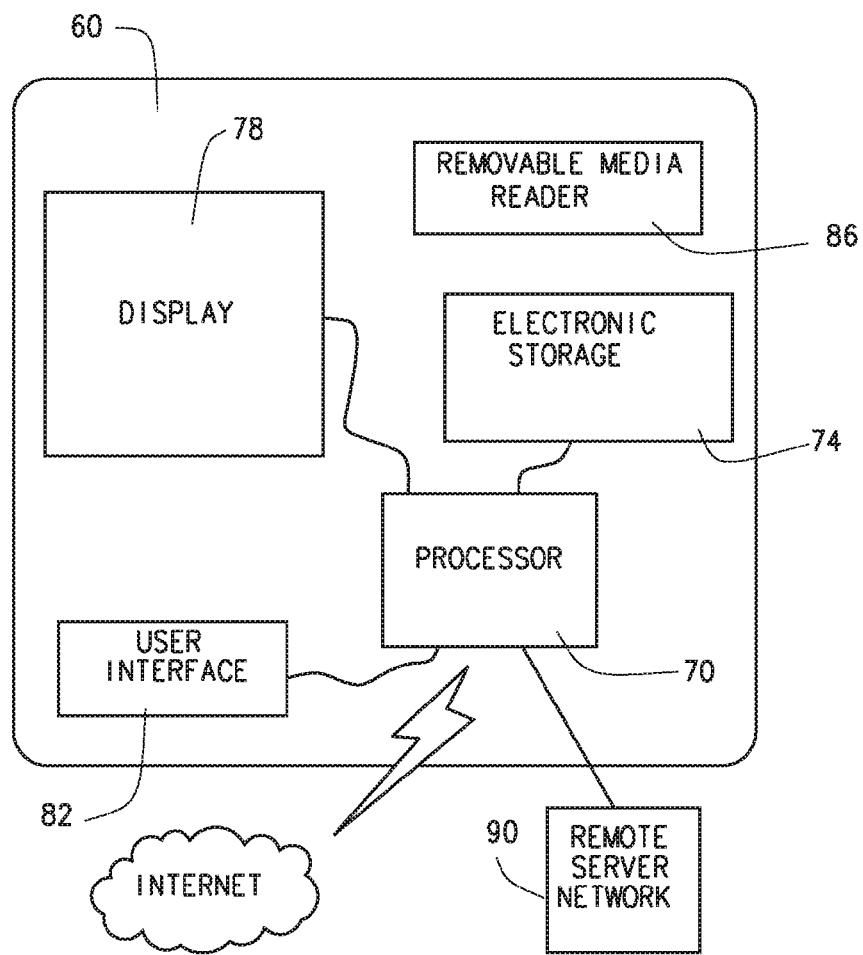

FIG. 6 is a block diagram of a computer based data analysis system of the system shown in FIG. 1, in accordance with various embodiments of the present disclosure.

Figure 7:
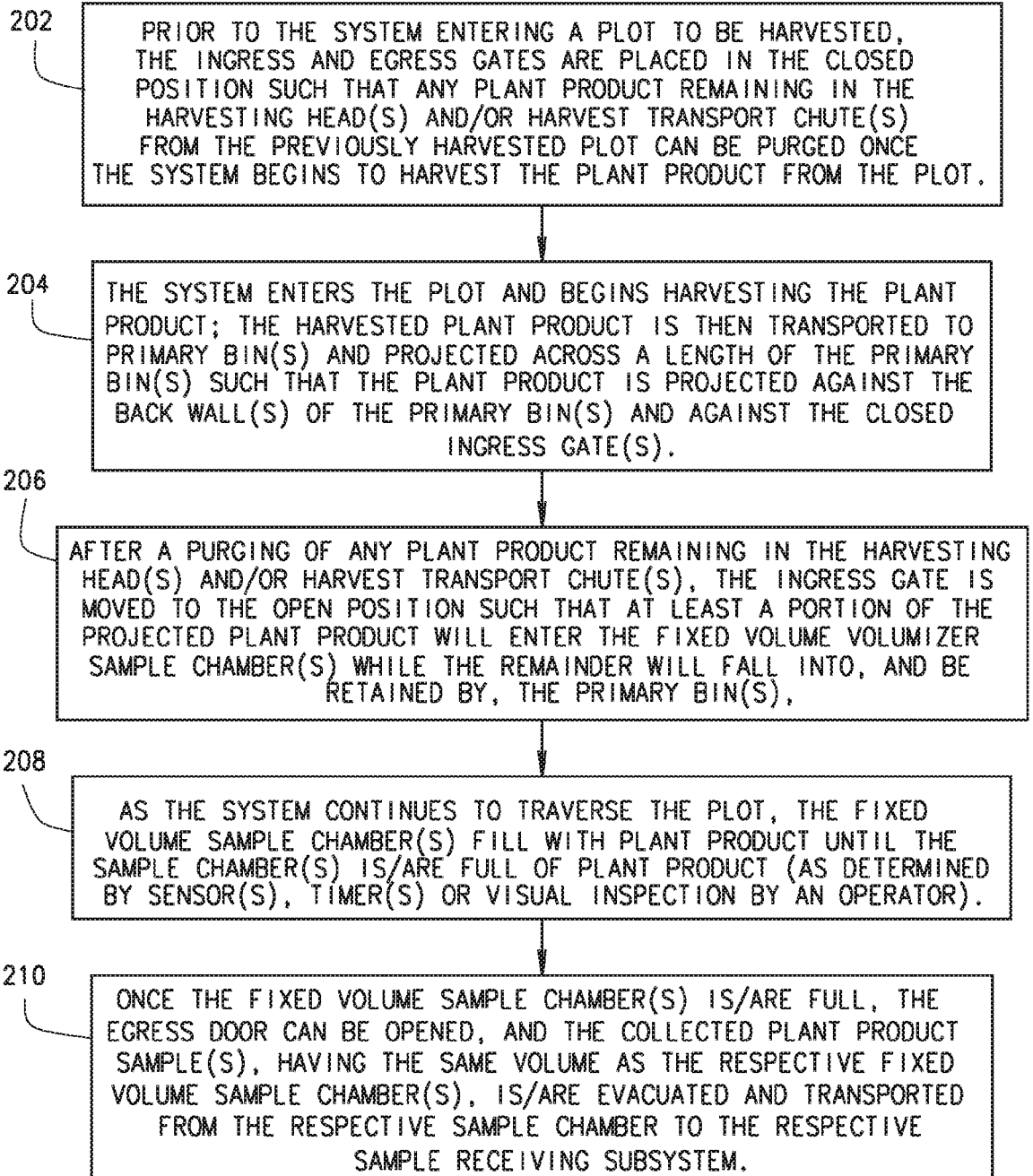
Figure 7A:
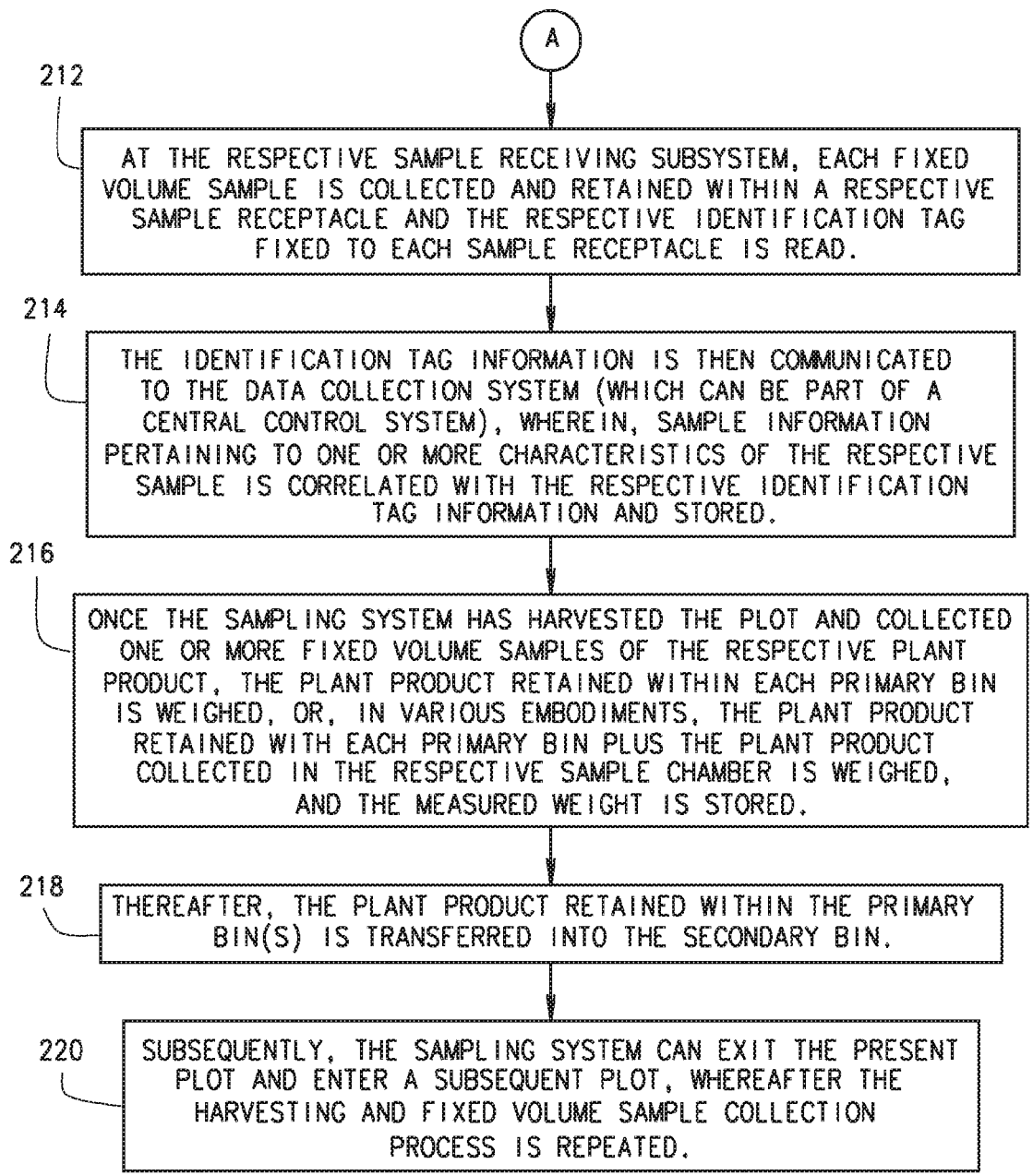

FIGS. 7 and 7A illustrate a flow chart exemplarily illustrating operation of the system shown in FIG. 1, in accordance with various embodiments of the present disclosure.

Corresponding reference numerals indicate corresponding parts throughout the several views of drawings.

DETAILED DESCRIPTION

The following description is merely exemplary in nature and is in no way intended to limit the present teachings, application, or uses. Throughout this specification, like reference numerals will be used to refer to like elements.

The embodiments disclosed below are not intended to be exhaustive or to limit the invention to the precise forms disclosed in the following detailed description. Rather, the embodiments are chosen and described so that others skilled in the art can utilize their teachings.

Unless otherwise defined, all technical and scientific terms used herein have the same meaning as commonly understood by one of ordinary skill in the art to which this disclosure belongs. The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps can be employed.

Although the terms first, second, third, etc. can be used herein to describe various elements, components, regions, devices, objects, sections, etc., these elements, components, regions, devices, objects, sections, etc., should not be limited by these terms. These terms may be used only to distinguish one element, component, region, device, object, section, etc., from another region, device, object, section etc., and do not necessarily imply a sequence or order unless clearly indicated by the context.

It should be understood that in any apparatus, system and/or method described herein as being structured and operable to being controlled by a computer based system and implemented by one or more computer programs executed by one or more processors, the computer programs include processor-executable instructions that are stored on a non-transitory, tangible, computer-readable medium. The computer programs can also include stored data. Non-limiting examples of the non-transitory, tangible, computer-readable medium are nonvolatile memory, magnetic storage, and optical storage.

Referring now to FIG. 1, the present disclosure provides a high-throughput sampling system 10 for sampling of a plant product. In various embodiments, the sampling system 10 generally includes a mobile platform 14, a plant product harvesting subsystem 22 connected to the mobile platform, and at least one sample volumizer 26. In various embodiments, the system 10 can include at least one sample evacuation duct 30, each sample evacuation duct 30 connected to a respective sample volumizer 26. As used herein the term plant product will be understood to mean the product derived from or produced by a plant. For example, the tissues or structures of the plant such as the flower, fruit, seed, grain, leaves, stems etc., produced by the plant. For example, seed cotton (or cotton bolls) from cotton plants, corn from corn plants, soy beans from soy plants, canola seeds from canola plants, wheat grain from wheat plants, or the leaves, stems, vegetables, seeds, grains, etc., from any other plant.

In general operation, a user can adjust a sample chamber 52 of each volumizer 26 to have a specific desired volume such that each volumizer 26 is able to collect and retain a volume of plant product that is specified by the user. Thereafter, as the sampling system 10 traverses a plot, via the mobile platform 14, the harvesting subsystem 22 harvests plant product from the plants growing in the plot, i.e., the harvesting subsystem 22 separates the plant product from the plants growing in the plot. The harvested plant product is then transported to an opening of one or more of the sample volumizers 26 where the plant product begins to fill each respective sample chamber 52. The plant product will continue to fill the sample chamber(s) 52 until the sample chamber(s) 52 is/are full, whereby the volume of collected plant product substantially equals the user specified internal volume of the sample chamber(s) 52. Once a volume specified by the user is contained in the sample chamber(s) 52, any further plant product directed toward the sample chamber 52 will either bounce back out of the respective sample chamber 52 and fall into one or more primary bin 18 of the sampling system 10, or it will replace a roughly equal-sized portion of plant product that may of fallen out of the respective sample chamber 52 and into the primary bin(s) 18. In this way, although additional plant product can be directed toward a filled sample chamber 52, it will not increase the amount of sample collected in each volumizer sample chamber 52. Thus, an operator need not monitor the volumizer(s) 26 to ensure that a desired amount of plant product sample is collected in each sample chamber 52. Moreover, as the system 10 continues to traverse the plot and harvest the plant product, the sample chambers(s) 52 will fill with the harvested plant product until the sample chamber(s) 52 is/are full. Importantly, when full, each sample chamber 52 will contain the user specified volume sample of the plant product.

In various embodiments, once the sample chamber(s) 52 is/are full, the collected specific volume sample(s) will be evacuated from the sample chamber(s) 52. In various embodiments, the sample(s) can be evacuated via the egress door 58 such that the sample merely drops out of the sample chamber 26 into a respective sample receptacle 36, while in various other embodiments, the sample(s) can be transported to a respective sample receptacle 36 via the sample evaluation duct(s) 30 to another location.

In various embodiments, the sample is transported to a sample receiving subsystem 34 of the sampling system 10. In such embodiments, upon being transported to the sample receiving subsystem 34, the sample(s), having the user specified volume, is/are collected and retained within a respective sample receptacle 36 (exemplarily shown in FIG. 4). Each sample receptacle 36 includes or is marked with an identification tag 38, whereafter information pertaining to one or more characteristics of the respective sample is correlated with the respective identification tag 38 and stored in a computer based data collection system 32 (FIG. 5) of the sampling system 10.

In various embodiments, all harvested plant product that is directed toward the volumizer(s) 26 after the volume of plant product specified by the user has been collected in each sample chamber 52 (i.e., when each sample chamber is full) will fall out of (e.g. bounce back out of) the volumizer(s) 26 and into, and be retained by, the primary bin(s) 18. In various implementations, each volumizer 26 can be connected to the back wall 18A of a respective primary bin 18. More specifically, in various embodiments, the each volumizer 26 is connected to the back wall 18A of a respective primary bin 18 at a location whereby the plant product that is blown or projected across the respective primary bin 18 (as described below) will be projected against the back wall 18A at the location where the respective volumizer 26 is connected. More specifically, in various implementations, each volumizer 26 can include an ingress door 54 that is movable between a Closed position, wherein at least a portion of the harvested plant product is projected against the Closed ingress door 54, and an Open position, wherein at least a portion of the harvested plant product is projected through the Open ingress door 54 into the sample chamber 52, as described further below. Hence, when the ingress door 54 is Open, and the plant product is projected across the primary bin(s) 18 and against the back wall(s) 18A, a portion of the projected plant product will enter the collection chamber(s) 52 while the remainder will fall into, and be retained by, the primary bin(s) 18. Once the collection chambers(s) 26 is/are full, the fixed volume sample(s) can be evacuated from the volumizer(s) 26 and transported, via the sample evaluation duct(s) 30 to the sample receiving subsystem 34.

Figure 2:
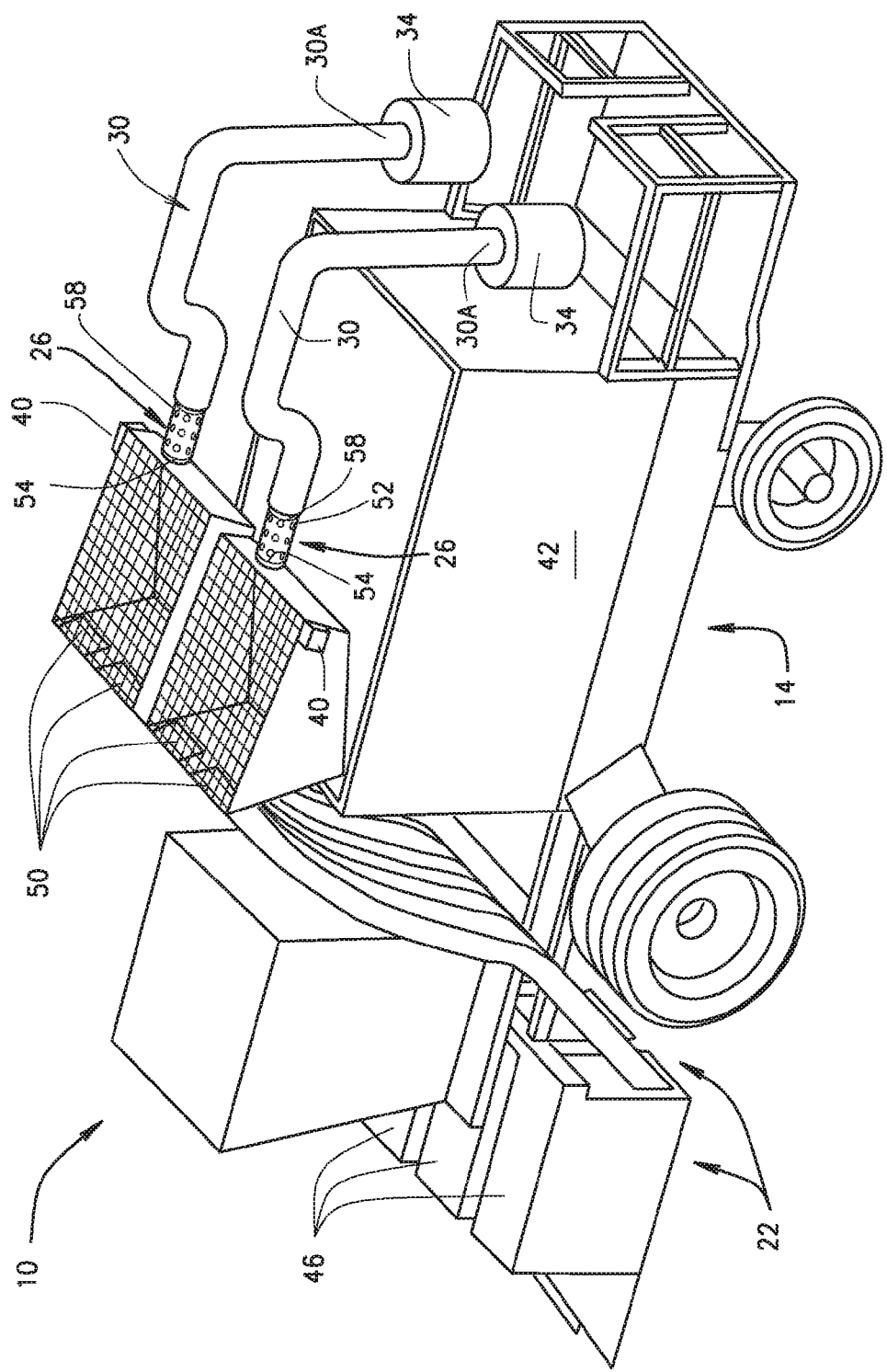
FIG. 2 is an isometric view of the system shown in FIG. 1 in accordance with various embodiments of the present disclosure.

Referring now to FIGS. 1, 2 and 3, in various embodiments, the harvesting subsystem 22 includes at least one harvesting head 46 and at least one harvest transport chute 50. Each harvesting head 46 is structured and operable to separate the plant product from the plurality of plants in the plot as the sampling system 10 traverses the plot. Each harvest transport chute 50 is fluidly connected to a respective harvesting head 46 and extends between the respective harvesting head 46 and a respective primary bin 18 such that the plant product separated from the plants can be conveyed from each harvesting head 46 and projected across (e.g., blown and/or thrown across) a length L of the respective primary bin 18 against the back wall 18A such that the separated plant product can be deposited in the respective primary bin 18 and fill the respective volumizer 26. The harvested plant product can be transported from the harvesting head(s) 46 to the primary bin(s) 18, via the harvest transport chute(s) 50, utilizing any suitable conveyance means, e.g., forced air, a conveyor belt, and/or a vacuum. In various embodiments the sampling system 10 includes a forced air source and venturi vacuum system (not shown) that generates a vacuum to transport the harvested plant product from the plants, through the harvesting head(s) 46 and into the harvest transport chute(s) 50. Thereafter, forced air transports the harvested plant product through the harvest transport chute(s) 50 and projects, shoots, or blows, the harvested plant product against the back wall(s) 18A of the primary bin(s) 18.

As described above, in various embodiments, each sample volumizer 26 is structured and operable to receive and collect a user specified volume sample of the plant product projected against the back wall 18A of the primary bin 18. Particularly, as best shown in FIG. 1, in various embodiments, each volumizer 26 comprises a hollow sample chamber 52 having an interior cavity with a volume equal to the specified fixed volume, an ingress door 54 disposed between the primary bin back wall 18A and an ingress end 52A of the sample chamber 52, and an egress door 58 disposed between an egress end 52B of the sample chamber 52 and the respective sample evacuation duct 30. Each sample chamber 52 can have any desired shape and size structured to have any desired specific fixed interior volume. For example, in various instances each sample chamber 52 can have a cylindrical shape having a diameter and length structured to provide an interior volume that can be calibrated to hold a specified total amount or volume of plant product, e.g., of 225 grams. Alternatively, it is envisioned that the egress door 58 can be selectively positionable within the sample chamber 52, such that the interior volume of the sample chamber 52 can be adjusted, whereby the fixed volume of the collected sample can be adjusted. Alternatively, it is envisioned that the interior volume of the sample chamber 52 can includes one or more plungers, valves, additional doors, flaps, etc., structured and operable to selectively adjust the interior volume of the sample chamber 52, and thus adjust the fixed amount of sample collected. Accordingly, when each sample chamber 52 is filled with the plant product, as described below, a fixed volume sample, e.g., a 225 gram sample, of the plant product will be collected in the sample chamber 52 and subsequently deposited into a respective sample receptacle 36.

As used herein, the term 'fixed', with regard to the volume of the sample(s) collected, i.e., fixed volume sample, will be understood to mean that the volume of the sample(s) collected can be selected and specified, i.e. fixed, to any desired volume. More particularly, the volumizer 26 can be structured or adjustably configured to have any selected and specified volume, whereby all samples collected will consistently and uniformly have substantially the same fixed volume. That is, the volume of each sample collected is fixed to a selected and specified value, e.g., 225 grams, based on the configured interior volume of the sample chamber 52. Hence, the sampling system 10 is structured and operable to collected a plurality of samples (as described herein), such that each sample will have substantially the same fixed volume, i.e., the same selected and specified volume, based on the interior volume of the sample chamber 52, wherein the sample chamber 52 can be structured or adjustably configured to have any desired interior volume.

The ingress door 54 can be transitioned between an Open and a Closed position. In various embodiments, the ingress door 54 can be placed in the Closed position to prevent the plant product projected across the length L of the primary bin 18 and against the back wall 18A from entering the sample chamber 52 such that all the harvested plant product will fall into and be retained within the primary bin 18. In various instances, the ingress door 54 is placed in the Closed position when the system 10 starts to traverse a plot and begins to harvest the plant product. This allows for a purging of any plant product that may remain in the harvesting head(s) 46 and/or harvest transport chute(s) 50 from the previously harvested plot and thereby prevents contamination between plots. Subsequently, after the purging of the previously harvested plant product, the ingress door 54 can be placed in Open position to allow the plant product from the presently harvested plot to enter and fill the fixed volume sample chamber 52.

Similarly, the egress door 58 can be transitioned between an Open and a Closed position. When the egress door 58 is in the Closed position, and the ingress door 54 is in the Open position, the plant product from the presently harvested plot that enters the fixed volume sample chamber 52 will be retained within and fill the fixed volume sample chamber 52. Once the sample chamber 52 is filled with plant product, the ingress door 54 can be moved to the Closed position such that all subsequently harvested plant product from the respective plot is deposited within the primary bin 18. Furthermore, once the sample chamber 52 is filled, the egress door 58 can be moved to the Open position, whereafter the fixed volume sample of the plant product is transported through the evacuation duct 30 and deposited into a respective sample receptacle 36.

Each plant product sample can be transported from the respective sample chamber 52 to the respective sample receptacle 36, via the evacuation duct(s) 30, utilizing any suitable conveyance means, e.g., forced air, a conveyor belt, and/or a vacuum. As described above, in various embodiments the sampling system 10 includes a forced air source and venturi vacuum system (not shown). In such embodiments, the forced air source and venturi vacuum system can be utilized to generate a vacuum and create air flow that is used to draw the plant product into the respective sample collection chamber 52, and/or retain the collected plant product within the sample collection chamber 52, and/or transport the collected fixed volume plant product sample from the respective sample chamber(s) 52, through the evacuation duct(s) 30 into the respective sample receptacle 36.

Additionally, in various instances of such forced air source and venturi vacuum embodiments, to provide proper air flow and vacuum within each sample collection chamber 52, each collection chamber includes a plurality of air vents, or holes, 64 (FIG. 1) that extend from the interior cavity of each respective sample collecting chamber 52 through the wall of the respective sample collection chamber 52 to the exterior ambient environment thereof. The air vents 64 allow air to flow through the respective sample collection chamber 52 and through the respective air vents 64 such that plant product is effectively and efficiently drawn into the respective sample collection chamber 52, and/or retained within the sample collection chamber 52, and/or transported the collected fixed volume plant product sample from the respective sample chamber(s) 52, through the evacuation duct(s) 30 into the respective sample receptacle 36.

Particularly, the air vents 64 allow the forced air source and venturi vacuum system to generate an air flow through each respective sample collection chamber 52, wherein at least a portion of the air flow includes air drawn into the respective sample collection chamber interior chamber from the ambient environment through the air vents 64. Alternatively or additionally, in various embodiments, the air vents 64 can allow at least a portion of the air flow generated by the forced air source and venturi vacuum system to flow from the interior cavity of each respective sample collection chamber 52, through the air vents 64, and into the exterior ambient environment. In various embodiments, the air vents 64 can extend from the interior cavity of a sample collection chamber 52 to the exterior ambient environment at substantially any angle relative to the wall of the sample collection chamber. In various embodiments, the holes extend through the wall of the sample collection chamber at 90 degrees relative to the wall of the sample collection chamber 52. While in various other embodiments, the air vents 64 are angled through the wall of the sample collection chamber 52. In such angled embodiments, the air vents 64 can extend through the wall at an angle of about 20° to 90° degrees relative to the wall of the sample collection chamber 52. In various embodiments, the interior rim of an air vent 64 can be beveled and/or smoothed where it transitions to the interior of the wall of the sample collection chamber 52 in order to reduce and/or prevent the plant product from snagging, hooking and/or otherwise attaching to the interior wall of the respective sample collection chamber 52.

In various embodiments, it is envisioned that each sample collection chamber 52 can include a screen, mesh or wide weave fabric barrier disposed within, over or under each air vent 64. Alternatively, it is envisioned that in various embodiments, each sample collection chamber 52 can include a screen, mesh or wide weave fabric sleeve disposed within or over the respective sample collection chamber 52. In yet other embodiments, it is envisioned that each sample collection chamber 52, or at least a portion of each sample collection chamber wall, can comprise or be fabricated of a screen, a mesh or a wide weave fabric.

The ingress and egress doors 54 and 58 can be transitioned between the Open and Closed position, via any suitable means of operation. For example, in various embodiments, movement of the ingress and egress doors 54 and 58 can be affected by actuators (e.g., electric, pneumatic or hydraulic actuators) whose operation is controlled by an operator of the system 10, e.g., an driver of the mobile platform 14. Alternatively, in various embodiments, movement of the ingress and egress doors 54 and 58 can be affected by actuators (e.g., an electric, pneumatic or hydraulic actuators) whose operation is automatically controlled by a computer based central control system 60 (exemplarily illustrated in FIG. 6) that is communicatively connected to one or more sensors and/or timers (not shown). In such instances, the sensor(s) and/or timer(s) determine when a sufficient amount of plant product has been purged such that the central control system 60 will Open the ingress door 54 and Close the egress door 58, and when the sample chamber is full such that the central control system 60 will Open the egress door 58. In such embodiments, the central control system 60 can be structured and operable to control the operation of a plurality, or all, of the operations and functions of the sampling system 10. Additionally, in such embodiments, the central control system 60 can include, comprise or be communicatively connected to the computer based data collection described above with regard to the correlation of the collected sample identification information with the respective sample receptacle identification tag 38.

As described above, once the sampling system 10 has harvested a plot and collected one or more fixed volume samples of the respective plant product, the plant product retained within each primary bin 18 can be weighed via a scale system 40 and then transferred into the larger secondary bin 42. In various embodiments, the cumulative weight of the plant product retained within each primary bin 18 plus the weight of a sample retained within the sample chamber 52 can be measured by the scale system 40. The system 10 will include a scale system 40 for each respective primary bin 18 and volumizer 26 combination. Each scale system 40 can comprise any component(s), device(s), mechanism(s), etc. structured and operable to measure the weight of the plant product retained within the respective primary bin 18, or the cumulative weight of plant product retained within the respective primary bin 18 and the plant product within the respective sample chamber 52. For example, in various embodiments, the scale system 40 can comprise one or more load cells. In such embodiments, each respective primary bin 18, and in various implementations each respective volumizer 26, can be suspended from, e.g., hang from, one or more load cells mounted to structural framework, beam, bars or braces mounted to the mobile platform 14. Alternatively, in various other embodiments, each respective primary bin 18, and in various implementations each respective volumizer 26, can be disposed on, e.g., sit on, one or more load cells mounted to structural framework, beam, bars, braces or platforms mounted to the mobile platform 14. The measured weight is subsequently stored in the data collection system 32 and cross-referenced to a plot number identifying the respective plot and/or a GPS position of the respective plot in the field.

Once the system 10 has harvested the plant product from a plot, the desired number of plant product samples have been collected and deposited into sample receptacles 36, and the weight of the plant product deposited within the primary bin(s) 18 (in various implementations, the weight of the plant product deposited within the primary bin(s) 18 plus the weight of the sample(s) in volumizer(s) 26) has been determined, and in various embodiments, after the plant product has been analyzed, a dump door 62 (exemplarily shown in FIG. 1) disposed in a bottom or side of each primary bin 18 can be Opened to transfer the harvested plant product from the primary bin 18 to the secondary bin 42. Thereafter, the dump door 62 can be Closed such that plant product harvested from a subsequent plot can be collected in the primary bin 18. FIG. 2 illustrates an exemplary embodiment of the system 10 wherein the primary bin(s) 18 can be disposed over the secondary bin 42 and the dump door(s) 62 can be disposed in the bottom of the primary bin(s) 18 such that when the dump door(s) is/are Opened the plant product within the primary bin(s) 18 falls into the secondary bin 42, via gravitational forces. Alternatively, in various other embodiments, as exemplarily illustrated in FIG. 3, the primary bin(s) 18 can be located behind or alongside of the secondary bin 42 and the dump door(s) 62 can be disposed laterally adjacent the secondary bin 42. In such embodiments, the plant product accumulated in the primary bin(s) 18 can be transferred to secondary bin 42 via forced air or other suitable conveyance means upon Opening of the dump door(s) 62.

Referring now to FIGS. 1, 2, 3 and 5, each sample receiving subsystem 34 is disposed at the outlet end 30A of a respective sample evacuation duct 30 and can receive and collect the fixed volume samples from the respective sample volumizer 26. The sample receiving subsystem 34 can additionally read the respective identification tag 38, and communicate the identification tag information to the data collection system 32, where the identification tag information is correlated with one or more characteristics of the respective sample and stored in the data collection system 32.

In various embodiments, the sample receiving subsystem 34 can be a manually operated system comprising one or more sample receptacles 36 and an identification label reader 66 that is communicatively connected (e.g., wired or wirelessly connected) to the computer based data collection system 32. In such embodiments, an operator rides on the back the mobile platform 14 and places a sample receptacle 36 at the outlet end 30A of each evacuation duct 30. Then, once a fixed volume plant product sample is collected in each volumizer 26 and deposited in the respective sample receptacle 36, the operator removes each filled sample receptacle 36 from the evacuation duct 30, closes or seals (e.g., heat seals) each sample receptacle 36, scans the respective identification label(s) 38, and places the filled sample receptacle(s) in a storage area (not shown) on the mobile platform 14. The scanned identification label information is communicated to the data collection system 32, where the identification label information is correlated with the sample information pertaining to one or more characteristics (e.g., weight, yield, quality, performance, etc., of the plant product) of the respective sample and stored in an electronic memory device of data collection system 32, and/or electronically transmitted to an electronic memory device at a location located remotely from the mobile platform 14. In various instances, the data collection system 32 can be locally located, i.e., located on the mobile platform 14, near the person removing and scanning the filled sample receptacles 36 such that the operator can enter various data and/or sample information related to each respective collected sample, whereafter the data and/or sample information is correlated with the respective receptacle identification label information. In various other instances, the data collection system 32 can be remotely located, whereby the received identification label information is automatically correlated with the respective sample information.

In various other embodiments, the sample receiving subsystem 34 can be an automated system comprising one or more sample receptacles 36 and a computer controlled or programmable device/system (not shown). In such embodiments, the computer controlled or programmable device/system is structured and operable to automatically place a sample receptacle 36 at the outlet end 30A of each evacuation duct 30, then, remove each filled sample receptacle 36 from the evacuation duct 30, close or seal (e.g., heat seal) each sample receptacle 36, scan the respective identification label(s) 38 via an identification label reader (not shown), and place the filled sample receptacle(s) 36 in a storage area (not shown) on the mobile platform 14. As described above, the scanned sample receptacle identification label information is communicated to the data collection system 32, where the identification label information is correlated with the sample information pertaining to one or more characteristics of the respective sample and stored in an electronic memory device of data collection system 32.

In various instances, the data collection system 32 can be locally located and communicatively connected to or part of the automated sample receiving subsystem 34, whereby the identification label information is automatically correlated with the respective sample information. In various other instances, the data collection system 32 can be remotely located, whereby the received identification label information is automatically correlated with the respective sample information. In various implementations, the automated sample receiving subsystem 34 can be controlled by the central control system 60. Alternatively, the automated sample receiving subsystem 34 can include a control module structured and operable to control the operations and functions described above. For example, the control module can include one or more of Application Specific Integrated Circuits (ASIC); electronic circuits; combinational logic circuits; field programmable gate arrays (FPGA); processors (shared, dedicated, or group) that execute code; other suitable hardware components that provide the described functionality; or a combination of some or all of the above, such as in a system-on-chip; or memory (shared, dedicated, or group) that store code executed by the processor(s).

The sample receptacle(s) 36 can be any receptacle that can be removably disposed at the outlet end 30A of a respective evacuation duct 30, and/or is suitable to have an identification label 38 affixed thereto, and/or is suitable for receiving and retaining the plant product samples. For example, in various embodiments the sample receptacle(s) 36 can be a closable and/or sealable paper, plastic or cloth bag; a closable and/or sealable paper, plastic or cloth envelope; or a closable and/or sealable cardboard or plastic container.

The identification labels 38 can be any label suitable for providing the sample receptacle identification label information. For example, the identification labels 38 can be radio frequency identification (RFID) labels, one-dimensional (1D) barcode labels, two-dimensional (2D) barcode labels, or any other suitable identification label. Similarly, the identification label reader, e.g., the identification label reader 66, can be any reader suitable for reading the sample receptacle identification labels 38. For example, the identification label reader a radio frequency identification (RFID) reader, a one-dimensional (1D) barcode reader, a two-dimensional (2D) barcode reader, or any other suitable identification label reader.

Referring now to FIG. 6, as described above, in various embodiments, the operation and functionality of all or part of the sampling system 10 can be controlled by the central control system 60. Generally, the central control system includes at least one processor 70 (shared, dedicated, or group) suitable to execute all software, programs, algorithms, etc., implemented to control the operation and functionality of all or part of the sampling system 10. The central control system 60 additionally includes at least one electronic storage device 74 that comprises a computer readable medium, such as a hard drive or any other electronic data storage device (shared, dedicated, or group) for storing such things as software packages or programs and algorithms, and for storing such other things as digital information, data, look-up tables, spreadsheets and databases. In various embodiments, the central control system 60 can further include a display 78 for displaying such things as information, data and/or graphical representations, and at least one user interface device 82, such as a keyboard, mouse, stylus, and/or an interactive touch-screen on the display 78. In various embodiments, the central control system 60 can still further include a removable media reader 86 for reading information and data from and/or writing information and data to removable electronic storage media such as floppy disks, compact disks, DVD disks, zip disks, flash drives or any other computer readable removable and portable electronic storage media. In various embodiments the removable media reader 86 can be an I/O port utilized to read external or peripheral memory devices such as flash drives or external hard drives.

As described above, in various embodiments, the central control system 60, e.g., the processor(s) 70, can be communicatively connected to the data collection system 32. In various embodiments, the central control system 60, e.g., the processor(s) 70, can be communicatively connectable to a remote server network 90, e.g., a local area network (LAN) or a wide area network (WAN), via a wired or wireless link. Accordingly, the central control system 60 can communicate with the remote server network 90 to upload and/or download data, information, algorithms, software programs, and/or receive operational commands. Additionally, in various embodiments, the central control system 60 can be structured and operable to access the Internet to upload and/or download and/or store (e.g., via the Cloud) data, information, algorithms, software programs, etc.

Referring now to FIG. 7, FIG. 7 provides a flow chart 200 illustrating an exemplarily sequence of events during operation of the high-throughput sampling system 10, in accordance with various embodiments of the present disclosure. Initially, prior to the system 10 entering a plot to be harvested, the ingress and egress doors 54 and 58 of the volumizer 26 are placed in the Closed position such that any plant product remaining in the harvesting head(s) 46 and/or harvest transport chute(s) 50 from the previously harvested plot can be purged once the system 10 enters and begins harvesting the plot, as indicated at 202. Thereafter, the system 10 enters the plot, via the mobile platform 14, and begins harvesting the plant product, via the harvesting head(s) 46. The harvested plant product is then transported to primary bin(s) 18, via the harvest transport chutes 50, and projected across the length L of the primary bin(s) 18 such that the plant product is projected against the back wall(s) 18A of the primary bin(s) 18 and against the Closed ingress door(s) 54, as indicated in 204. After the purging of any plant product remaining in the harvesting head(s) 46 and/or harvest transport chute(s) 50 from the previously harvested plot, the ingress door 54 is moved to the Open position such that at least a portion of the plant product projected across the primary bin(s) 18 will enter the respective fixed volume volumizer sample chamber(s) 52 while the remainder will fall into, and be retained by, the primary bin(s) 18, as indicated at 206.

As the system 10 continues to traverse the plot, the ingress door 54 remains Open, the egress door 58 remains Closed, and the fixed volume sample chamber(s) 52 continues to fill with plant product. Once the fixed volume sample chamber(s) 52 is/are full of plant product (as determined by sensor(s), timer(s) or visual inspection by an operator), the egress door 58 can be Opened. Thereafter, the collected plant product sample(s), having the same volume as the respective fixed volume sample chamber(s) 52, is/are evacuated from the sample chamber(s) 52 and transported through the respective sample evacuation duct 30 to the respective sample receiving subsystem 34, as indicated at 208 and 210. Although it is not necessary, it is envisioned that in various implementations, once the sample chamber(s) 52 is/are full, the ingress door 54 can be moved to the Closed position prior to the egress door 58 being Opened. At the respective sample receiving subsystem 34, each fixed volume sample is collected and retained within a respective sample receptacle 36 and the respective identification tag 38 fixed to each sample receptacle 36 is read, via a suitable identification tag reader, e.g., identification tag reader 66, as indicated at 212. The identification tag information is then communicated to the data collection system 32, which, as described above, can be part of the central control system 60. Thereafter, sample information pertaining to one or more characteristics of the respective sample is correlated with the respective identification tag information 38 and stored in the data collection system 32, as indicated at 214.

Once the sampling system 10 has harvested the plot and collected one or more fixed volume samples of the respective plant product, the plant product retained with each primary bin 18 can be weighed, or, in various embodiments, the plant product retained with each primary bin 18 plus the plant product collected in the respective sample chamber 52 can be weighed, via a scale system 40, and the measured weight can be stored in the data collection system 32, as indicated at 216. Thereafter, the plant product retained within the primary bin(s) 18 is transferred into the secondary bin 42, via the respective dump doors 62, as indicated at 218. Subsequently, the system 10 can exit the present plot and enter a subsequent plot, whereafter the harvesting and fixed volume sample collection process is repeated, as indicated at 220.

It is envisioned that in various embodiments, the sampling system 10 can be structured such that it does not include the primary bin 18, the corresponding back wall, and/or the ingress door(s) 54 of the volumizer(s) 26. In such embodiments, it is envisioned that the system 10 can harvest the plant product, as described above, and fill each sample chamber 52 having an open ingress end 52A (i.e., absent the ingress door 54) with the specified volume of plant product from the targeted plants in a plot, capture information about each sample, and then discard each sample. Additionally, it is envisioned that in various embodiments, the volumizer 26 can be positioned below or within the flow of harvested plant product, and not mounted to a rear wall of the primary bin 18 or secondary bin 42, such that the harvested plant product will fill the volumizer sample chamber(s) 52. Or, alternatively, it is envisioned that in various embodiments, the harvested plant product can diverted into a chute with a volumizer 26 disposed at an end thereof, whereby a sensor detects when to turn off the diverter when the volumizer is full.

In various embodiments, the collected samples of plant product can be analyzed and the analysis data can be used to determine various phenotype and/or genotype traits and/or characteristic of the respective plant product. For example, in various embodiments, the plant product can be cotton wherein the fixed volume samples comprise cotton bolls. In such embodiments, the collected fixed volume samples of cotton bolls can be analyzed to determine such things as lint percent, gin turnout, staple length, etc.

For example, it is envisioned that in various instances, the structures, features, and functions of the sampling system 10, described above, can be implemented in conjunction with structures, features, and functions of the system described in PCT Application PCT/US2015/052133, titled High Throughput Methods of Analyzing Seed Cotton Using X-Ray Imaging, filed Sep. 25, 2015, and corresponding U.S. Provisional Application 62/055,861, filed Aug. 15, 2014, the disclosure of each being incorporated by reference herein in their entirety. For example, it is envisioned that various structures, features and function of the systems and methods described in PCT Application PCT/US2015/052133 can be incorporated into the high-throughput sampling system 10 described above. For example, in various instances, various structures, devices, systems, etc., described in PCT/US2015/052133 can be disposed on the mobile platform 14, and the functions thereof incorporated into the functions of the sampling system 10 described above. For example, in such instances, in addition to functions of the sampling system 10 described above, the sampling system 10 could analyze a sample of cotton at some point before, during, or after the sample is collected in a sample collection chamber 52. For example, once a sample of cotton has collected in a sample collection chamber 52, the sample could be subjected to analysis by an X-ray device similar to that described in PCT/US2015/052133 to detect and/or score the sample for any trait detectable by the system that the user wishes to know.

In various embodiments, a sample collected in the volumizer 26, e.g., in the sample collection chamber 52, can be subjected to X-ray analysis. This analysis can involve moving the sample through a field of view of an image data generation assembly, or it can involve moving an image data generation assembly relative to the sample, as described in PCT/US2015/052133. In various embodiments, the sample of plant product in the sample collection chamber 52 can be rotated within the field of view of the image data generation assembly and in various embodiments the image data generation assembly can revolve around the sample collection chamber 52 to capture information desired by the user. In certain embodiments, analyses of samples of plant product can take place before or after the sample has left the sample collection chamber 52. For example, a sample collected in a sample receptacle 36 can be subjected to analysis using a device and/or method disclosed in PCT/US2015/052133.

Similarly, other methods known in the art to be useful for analyzing plant products could be adapted to fit onboard the mobile platform 14 and used to analyze samples of the plant. For example, imaging devices and methods useful for analyzing plant products (e.g. NIR, hyperspectral imaging, mass flow, capacitance mass flow, etc.) could be used to assess the characteristics of a sample of plant product as it moves through the high-throughput sampling system 10 and/or at certain points therein. In various embodiments, the sample of plant product in the sample collection chamber 52 can be rotated within the field of view of the imaging system to collect desired data, and in various embodiments components of the imaging system can revolve around the sample collection chamber 53 to capture information desired by the user. In various embodiments, analyses of samples of plant product can take place before or after the sample has left the sample collection chamber 52. For example, a sample collected in the sample receptacle 36 can be subjected to analysis while onboard the mobile platform 14, or after the sample has left the mobile platform. In various examples, it is envisioned that samples of plant product could be analyzed by non-imaging-based methods as well. For example, it is envisioned that a sample of plant tissue could be collected while plant product moves through the high-throughput sampling system 10. For example, a subsample of a sample in a sample collection chamber 52 can be extracted and that subsample subjected to a chemical, biochemical, physical, or genetic test known in the art to be useful for assaying plant material (e.g. PCR, sequencing, protein profiling, carbohydrate analysis, etc.) either onboard the mobile platform 14, are at a remote location. Thus, the devices, systems, and methods described herein could be used to genotype and/or phenotype plants growing in a plot in combination with any methods known in the art for assaying plant products.

Additionally, in various embodiments, it is envisioned that the sampling system 10, described above, can be a totally automated 'Smart' system, such as the system described in PCT Application PCT/US2015/045301, titled Apparatus And Methods For In-Field Data Collection And Sampling, filed Aug. 14, 2015, and corresponding U.S. Provisional Application 62/037,968, filed Aug. 15, 2014, the disclosure of each being incorporated by reference herein in their entirety. Particularly, it is envisioned that the systems and method described in PCT Application PCT/US2015/045301 can incorporate the systems and methods described above, and vice-versa, to collect one or more plant product sample(s), analyze the collected sample(s), make a decision about a treatment application at the site or on a plant, and apply a treatment—all from the same platform. Also, that the sample(s) and any information regarding the sample(s), generated by the respective system, could be combined with any data or information collected from an "analytics suite", such as that described in PCT Application PCT/US2015/045301, (e.g., cameras, soil samples, etc., disposed on a mobile platform 14) to assist in this process.

The description herein is merely exemplary in nature and, thus, variations that do not depart from the gist of that which is described are intended to be within the scope of the teachings. Moreover, although the foregoing descriptions and the associated drawings describe example embodiments in the context of certain example combinations of elements and/or functions, it should be appreciated that different combinations of elements and/or functions can be provided by alternative embodiments without departing from the scope of the disclosure. Such variations and alternative combinations of elements and/or functions are not to be regarded as a departure from the spirit and scope of the teachings.

What is claimed is:

1. A sampling system for high-throughput sampling of a plant product, said system comprising:
   a mobile platform;
   a harvesting subsystem connected to the mobile platform, the harvesting subsystem comprising:
      at least one harvesting head structured and operable to separate plant product from a plurality of plants in a plot as the sampling system traverses the plot; and
      at least one harvest transport chute, each of the at least one harvest transport chute extending from a respective harvesting head; and
   at least one sample volumizer disposed opposite an outlet end of the at least one harvest transport chute and in a flow of plant product as the plant product is transported through the harvesting system such that each of the at least one sample volumizer located to receive and collect a sample of the plant product projected from the at least one harvest transport chute;
   at least one primary bin disposed adjacent an ingress end of the at least one sample volumizer such that plant product projected from the at least one harvest transport chute not received and collected by the at least one sample volumizer will fall into the at least one primary bin; and
   at least one sample evacuation duct, each of the at least one sample evacuation duct connected to a respective sample volumizer.

2. The system of claim 1 further comprising at least one sample receiving subsystem, each of the at least one sample receiving subsystem disposed at an outlet end of a respective sample evacuation duct and structured and operable to receive and collect at least one sample from the respective sample volumizer.

3. The system of claim 1, wherein the at least one primary bin is disposed between the outlet end of the at least one harvest transport chute and the ingress end of the at least one sample volumizer such that the plant product projected from at least one harvest transport chute is projected across a length of the at least one primary bin toward the ingress end of the at least one sample volumizer.

4. The system of claim 1 further comprising at least one scale subsystem, each of the at least one scale subsystem operably connected to at least one sample volumizer and structured and operable to measure the weight of at least the plant product collected in at least one sample volumizer.

5. The system of claim 1 further comprising at least one scale subsystem, each of the at least one scale subsystem operably connected to a respective primary bin and structured and operable to measure a weight of at least the plant product collected in each respective primary bin.

6. The system of claim 5, wherein each volumizer comprises:
a sample chamber having an interior volume; and
at least one of:
an ingress door disposed between the respective primary bin back wall and an ingress end of the sample chamber; or
an egress door disposed between an egress end of the sample chamber and the respective sample evacuation duct, wherein the ingress and egress doors are structured and operable to open and close to allow plant product projected across the length of the respective primary bin to enter and fill the sample chamber in order to collect a sample having the specified volume, and then allow the collected sample to be conveyed from the sample chamber to the respective sample receiving subsystem.

7. The system of claim 6 wherein the interior volume of the sample chamber is adjustable.

8. The system of claim 6 further comprising a secondary bin disposed adjacent the at least one primary bin and structured and operable to receive plant product deposited in the at least one primary bin, and the at least one primary bin comprises a dump door operable to retain the plant product within the at least one primary bin when in a Closed position and to allow the plant product to be transferred from the at least one primary bin to the secondary bin when in an Open position.

9. The system of claim 1, wherein each of the at least one sample receiving subsystem comprises:
a plurality of manually operated sample receptacles structured and operable to receive and retain a respective collected sample, each sample receptacle having an identification label attached thereto, each identification label comprising identification information; and
an identification label reader structured and operable to read the identification information of each identification label and transmit the identification information to a computer based system where the identification information is stored and correlated with one or more characteristics of the collected sample retained within the respective sample receptacle.

10. The system of claim 1, wherein each of the at least one sample receiving subsystem comprises and automated system structured and operable to:
receive each collected sample and deposit each collected sample in a respective sample receptacle, wherein each sample receptacle has an identification label attached thereto, each identification label comprising identification information; and
read the identification information of each identification label and transmit the identification information to a computer based system where the identification information is stored and correlated with one or more characteristics of the collected sample retained within the respective sample receptacle.

11. The system of claim 1 further comprising a device capable of capturing at least one of information or data about the plant product retained within the volumizer before the contents are evacuated from the volumizer.

12. The system of claim 1 further comprising at least one of a computerized geo-referencing system, a computerized global positioning system, or a computerized plot coordinate system structured and operable to record a location where each sample is collected and associate that position with any other data and information about the location, including identifying the germplasm from which the sample was collected.

13. A sampling system for high-throughput sampling of a plant product, said system comprising:
a mobile platform;
a harvesting subsystem connected to the mobile platform, the harvesting subsystem comprising:
at least one harvesting head structured and operable to separate plant product from a plurality of plants in a plot as the sampling system traverses the plot; and
at least one harvest transport chute, each of the at least one harvest transport chute extending from a respective harvesting head; and
at least one sample volumizer disposed opposite an outlet end of the at least one harvest transport chute such that each of the at least one sample volumizer is located to receive and collect a sample of the plant product projected from the at least one harvest transport chute, and
at least one primary bin disposed adjacent an ingress end of the at least one sample volumizer such that plant product projected from the at least one harvest transport chute not received and collected by the at least one sample volumizer will fall into the at least one primary bin.

14. The system of claim 13 further comprising at least one sample receiving subsystem, each of the at least one sample receiving subsystem disposed at an outlet end of a respective sample evacuation duct connected to a respective sample volumizer, each of the at least one sample receiving subsystem structured and operable to receive and collect at least one sample from the respective sample volumizer.

15. The system of claim 13, wherein the at least one primary bin is disposed between the outlet end of the at least one harvest transport chute and the ingress end of the at least one sample volumizer such that the plant product projected from the at least one harvest transport chute is projected across a length of the at least one primary bin toward the ingress end of the at least one sample volumizer.

16. The system of claim 13 further comprising at least one scale subsystem, each of the at least one scale subsystem operably connected to at least one sample volumizer and structured and operable to measure the weight of at least the plant product collected in at least one sample volumizer.

17. The system of claim 13 further comprising at least one scale subsystem, each of the at least one scale subsystem operably connected to a respective primary bin and structured and operable to measure a weight of at least the plant product collected in each respective primary bin.

18. The system of claim 17, wherein each of the at least one sample volumizer comprises:
a sample chamber having an interior volume;
an ingress door disposed between the at least one primary bin back wall and an ingress end of the sample chamber; and an egress door disposed between an egress end of the sample chamber and the respective sample evacuation duct, wherein the ingress and egress doors are structured and operable to open and close to allow plant product projected across the length of the respective primary bin to enter and fill the sample chamber in order to collect a sample having the specified volume, and then allow the collected sample to be conveyed from the sample chamber to the respective sample receiving subsystem.

19. The system of claim 18 wherein the interior volume of the sample chamber is adjustable.

20. The system of claim 18 further comprising a secondary bin disposed adjacent the at least one primary bin and structured and operable to receive plant product deposited in the at least one primary bin, and the at least one primary bin comprises a dump door operable to retain the plant product within the at least one primary bin when in a Closed position and to allow the plant product to be transferred from the at least one primary bin to the secondary bin when in an Open position.

21. The system of claim 13, wherein each of the at least one sample receiving subsystem comprises:
   a plurality of manually operated sample receptacles structured and operable to receive and retain a respective collected sample, each sample receptacle having an identification label attached thereto, each identification label comprising identification information; and
   an identification label reader structured and operable to read the identification information of each identification label and transmit the identification information to a computer based system where the identification information is stored and correlated with one or more characteristics of the collected sample retained within the respective sample receptacle.

22. The system of claim 13, wherein each of the at least one sample receiving subsystem comprises an automated system structured and operable to:
   receive each collected sample and deposit each collected sample in a respective sample receptacle, wherein each sample receptacle has an identification label attached thereto, each identification label comprising identification information; and
   read the identification information of each identification label and transmit the identification information to a computer based system where the identification information is stored and correlated with one or more characteristics of the collected sample retained within the respective sample receptacle.

23. A sampling system for high-throughput sampling of plant product, said system comprising:
   a mobile platform;
   at least one primary bin disposed on the mobile platform;
   a harvesting subsystem connected to the mobile platform, the harvesting subsystem comprising:
      at least one harvesting head structured and operable to separate plant product from a plurality of plants in a plot as the sampling system traverses the plot; and
      at least one harvest transport chute, each of the at least one harvest transport chute extending between a respective harvesting head and a respective primary bin such that the plant product separated from the plants is capable of being conveyed from the at least one harvesting head and projected across a length of the at least one primary bin toward a back wall of the at least one primary bin such that the separated plant product is capable of being can be deposited in the at least one primary bin;
   at least one sample volumizer connected to the back wall of each of the at least one primary bin opposite an outlet end of the at least one harvest chute, each of the at least one sample volumizer located to receive and collect a sample of the plant product projected toward the back wall of the at least one primary bin such that plant product projected from the at least one harvest transport chute not received and collected by the at least one sample volumizer will fall into the at least one primary bin, each sample having a specified volume;
   at least one sample evacuation duct, each of the at least one sample evacuation duct connected to a respective sample volumizer; and
   at least one sample receiving subsystem, each of the at least one sample receiving subsystem disposed at an outlet end of a respective sample evacuation duct and structured and operable to receive and collect at least one sample from the respective sample volumizer.

24. The system of claim 23 further comprising at least one scale subsystem, each of the at least one scale subsystem operably connected to a respective primary bin and structured and operable to measure a weight of at least the plant product collected in each respective primary bin.

25. The system of claim 24, wherein each of the at least one sample volumizer comprises:
   a sample chamber having an interior volume equal to the specified volume;
   an ingress door disposed between the at least one primary bin back wall and an ingress end of the sample chamber; and
   an egress door disposed between an egress end of the sample chamber and the respective sample evacuation duct, wherein the ingress and egress doors are structured and operable to open and close to allow plant product projected across the length of the respective primary bin to enter and fill the sample chamber in order to collect a sample having the specified volume, and then allow the collected sample to be conveyed from the sample chamber to the respective sample receiving subsystem.

26. The system of claim 25 further comprising a secondary bin disposed adjacent the at least one primary bin and structured and operable to receive plant product deposited in the at least one primary bin, and the at least one primary bin comprises a dump door operable to retain the plant product within the at least one primary bin when in a Closed position and to allow the plant product to be transferred from the at least one primary bin to the secondary bin when in an Open position.

27. The system of claim 23, wherein each of the at least one sample receiving subsystem comprises:
   a plurality of manually operated sample receptacles structured and operable to receive and retain a respective collected sample, each sample receptacle having an identification label attached thereto, each identification label comprising identification information; and
   an identification label reader structured and operable to read the identification information of each identification label and transmit the identification information to a computer based system where the identification information is stored and correlated with one or more characteristics of the collected sample retained within the respective sample receptacle.

28. The system of claim 23, wherein each of the at least one sample receiving subsystem comprises and automated system structured and operable to:
- receive each collected sample and deposit each collected sample in a respective sample receptacle, wherein each sample receptacle has an identification label attached thereto, each identification label comprising identification information; and
- read the identification information of each identification label and transmit the identification information to a computer based system where the identification information is stored and correlated with one or more characteristics of the collected sample retained within the respective sample receptacle.

* * * * *